US010039613B2

(12) United States Patent
Hartmann et al.

(10) Patent No.: US 10,039,613 B2
(45) Date of Patent: Aug. 7, 2018

(54) METHOD FOR LOCALIZING AN IMAGING DEVICE WITH A SURGICAL NAVIGATION SYSTEM

(75) Inventors: Steven L. Hartmann, Superior, CO (US); Robert Teichman, Lafayette, CO (US); Laurent Verard, Superior, CO (US)

(73) Assignee: Surgical Navigation Technologies, Inc., Louisville, CO (US)

( * ) Notice: Subject to any disclaimer, the term of this patent is extended or adjusted under 35 U.S.C. 154(b) by 1809 days.

(21) Appl. No.: 11/713,113

(22) Filed: Mar. 1, 2007

(65) Prior Publication Data
US 2008/0214922 A1   Sep. 4, 2008

(51) Int. Cl.
| A61B 5/05 | (2006.01) |
| A61B 90/00 | (2016.01) |
| A61B 34/10 | (2016.01) |
| A61B 34/20 | (2016.01) |
| A61B 34/00 | (2016.01) |

(52) U.S. Cl.
CPC ............. *A61B 90/36* (2016.02); *A61B 34/20* (2016.02); *A61B 90/37* (2016.02); *A61B 2034/102* (2016.02); *A61B 2034/2051* (2016.02); *A61B 2034/2074* (2016.02); *A61B 2034/256* (2016.02); *A61B 2090/363* (2016.02); *A61B 2090/364* (2016.02); *A61B 2090/367* (2016.02); *A61B 2090/376* (2016.02)

(58) Field of Classification Search
CPC . A61B 19/52; A61B 19/5225; A61B 19/5244; A61B 2019/502; A61B 2019/5238
See application file for complete search history.

(56) References Cited

U.S. PATENT DOCUMENTS

| 5,592,939 | A | 1/1997 | Martinelli |
| 5,740,808 | A | 4/1998 | Panescu et al. |
| 5,913,820 | A | 6/1999 | Bladen et al. |
| 6,285,902 | B1 * | 9/2001 | Kienzle, III ............. A61B 6/12 378/20 |
| 6,381,485 | B1 | 4/2002 | Hunter et al. |
| 6,474,341 | B1 | 11/2002 | Hunter et al. |

(Continued)

FOREIGN PATENT DOCUMENTS

| EP | 1181897 | 2/2002 |
| WO | WO-0056215 | 9/2000 |
| WO | WO-04001569 | 12/2003 |

OTHER PUBLICATIONS

International Search Report for PCT/US2008/002745 dated Aug. 25, 2008.

(Continued)

*Primary Examiner* — James Kish
(74) *Attorney, Agent, or Firm* — Harness Dickey

(57) ABSTRACT

The position of an imaging device can be determined at least in part with a movement portion of the imaging device. The imaging device can be moved relative to the patient to obtain image data of the patient at different perspectives or angles. The image data obtained of the patient can be displayed with a display device at various perspectives and a tracked position of the instrument can be displayed at the appropriate perspective or a selected perspective relative to the image data with the display device based upon a known position of the imaging device.

26 Claims, 3 Drawing Sheets

(56) References Cited

U.S. PATENT DOCUMENTS

2002/0049378 A1* 4/2002 Grzeszczuk ........... A61B 90/36
                                                    600/427
2003/0191394 A1* 10/2003 Simon et al. ................ 600/473
2004/0215071 A1  10/2004 Frank et al.
2005/0085720 A1   4/2005 Jascob et al.
2005/0163279 A1   7/2005 Mitschke et al.

OTHER PUBLICATIONS

Communication pursuant to Article 94(3) EPC dated Sep. 16, 2014 for EP Application No. 08726307.5-1654.
Communication pursuant to Article 94(3) EPC dated Jul. 3, 2015 for EP Application No. 08726307.5-1654.

* cited by examiner

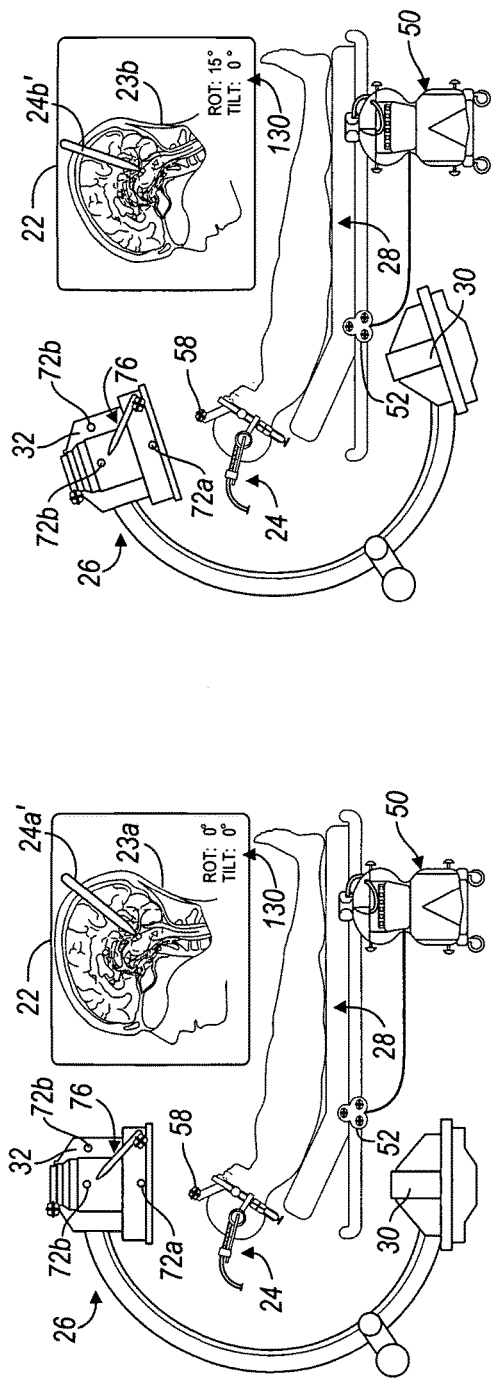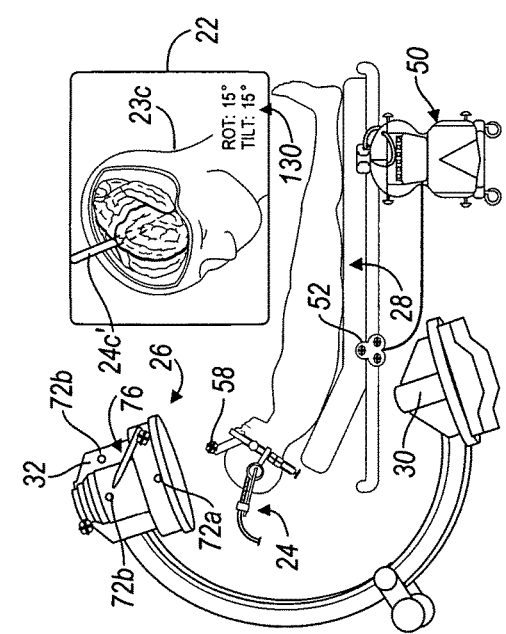
FIG. 3A
FIG. 3B
FIG. 3C

METHOD FOR LOCALIZING AN IMAGING DEVICE WITH A SURGICAL NAVIGATION SYSTEM

FIELD

The present disclosure is directed to a surgical navigation system, and particularly to a navigation system that employs an imaging system to obtain image data of a patient.

BACKGROUND

The statements in this section merely provide background information related to the present disclosure and may not constitute prior art.

Surgical procedures can be performed on a patient for various purposes. A procedure can be performed in various manners. Because many procedures are performed within the patient's anatomy, it is desirable to provide a system that allows a determination of a position of an instrument or an implant relative to the patient during an operative procedure.

Imaging devices can provide image data of portions of the patient, both internal and external. For example, a fluoroscope can be provided to obtain image data of a selected portion of the patient's anatomy. Generally, however, the fluoroscope can provide image data for viewing on a display. The image data, however, must be registered relative to the patient's anatomy to determine a position of an instrument relative to the image data of the patient.

Therefore, it is desirable to provide a system that allows for ease and efficiency of determining a position of an instrument relative to the patient for viewing on a display. This can assist in determining a position of the instrument or implant relative to the patient during an operative procedure.

SUMMARY

A system is disclosed that is operable to determine a position of an imaging device relative to a patient to assist in performing a navigated procedure. The imaging device can include an isocentric C-arm imaging device. The isocentric C-arm device can provide image data of a patient produced by x-ray emissions for display on a human readable display. The position of the isocentric C-arm can be determined based upon an baseline or tracked location of the isocentric C-arm and a known movement of the isocentric C-arm based upon a control system for the isocentric C-arm.

According to various embodiments a navigation system to navigate a procedure relative to an anatomy is taught. The navigation system can include an imaging device operable to capture image data of the anatomy and an imaging device processor operable to determine a baseline position and a current position relative to the baseline position. A tracking system and an instrument operable to be tracked with the tracking system relative to the anatomy is also disclosed. A navigation processor can determine the position of the instrument relative to the anatomy and a display device can display the obtained image data and an icon representing the instrument relative to the image data on the display device based at least in part on the determined position of the imaging device. The icon is operable to be displayed on the display device relative to the image data corresponding to the position of the instrument relative to the anatomy and the appropriate perspective.

According to various embodiments a navigation system to navigate a procedure to be performed in an anatomy is taught. The navigation system can include an imaging system including an image collection portion, a position selection portion operable to move the image collection portion between a first position and a second position, and a position selection portion processor operable to determine the first position of the image collection portion and a change to the second position of the image collection portion. A tracking system is taught including a localization system and a localization member operable to be localized with the localization system. An instrument can be tracked with the tracking system relative to the anatomy. Also, a navigation processor can determine a position of the instrument relative to the anatomy and the image collection portion.

According to various embodiments a method of performing a navigated procedure on an anatomy with an instrument is taught. The method can include providing an imaging device relative to the anatomy, determining an baseline position of the imaging device with an imaging device processor, moving the imaging device relative to the anatomy to a second position from the baseline position, and determining a change in position of the imaging device after moving the imaging device to the second position. An instrument can be tracked relative to the anatomy. Image data can be obtained of the anatomy with the imaging device at the second position. A position of the instrument relative to the obtained image data from a selected perspective based at least in part on the determined change in position of the imaging device after moving the imaging device can also be determined.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 3A-3C illustrate an imaging device in various orientations relative to a patient and a display device displaying image data from the various orientations.

DETAILED DESCRIPTION

The following description is merely exemplary in nature and is not intended to limit the present disclosure, application, or uses.

Figure 1:
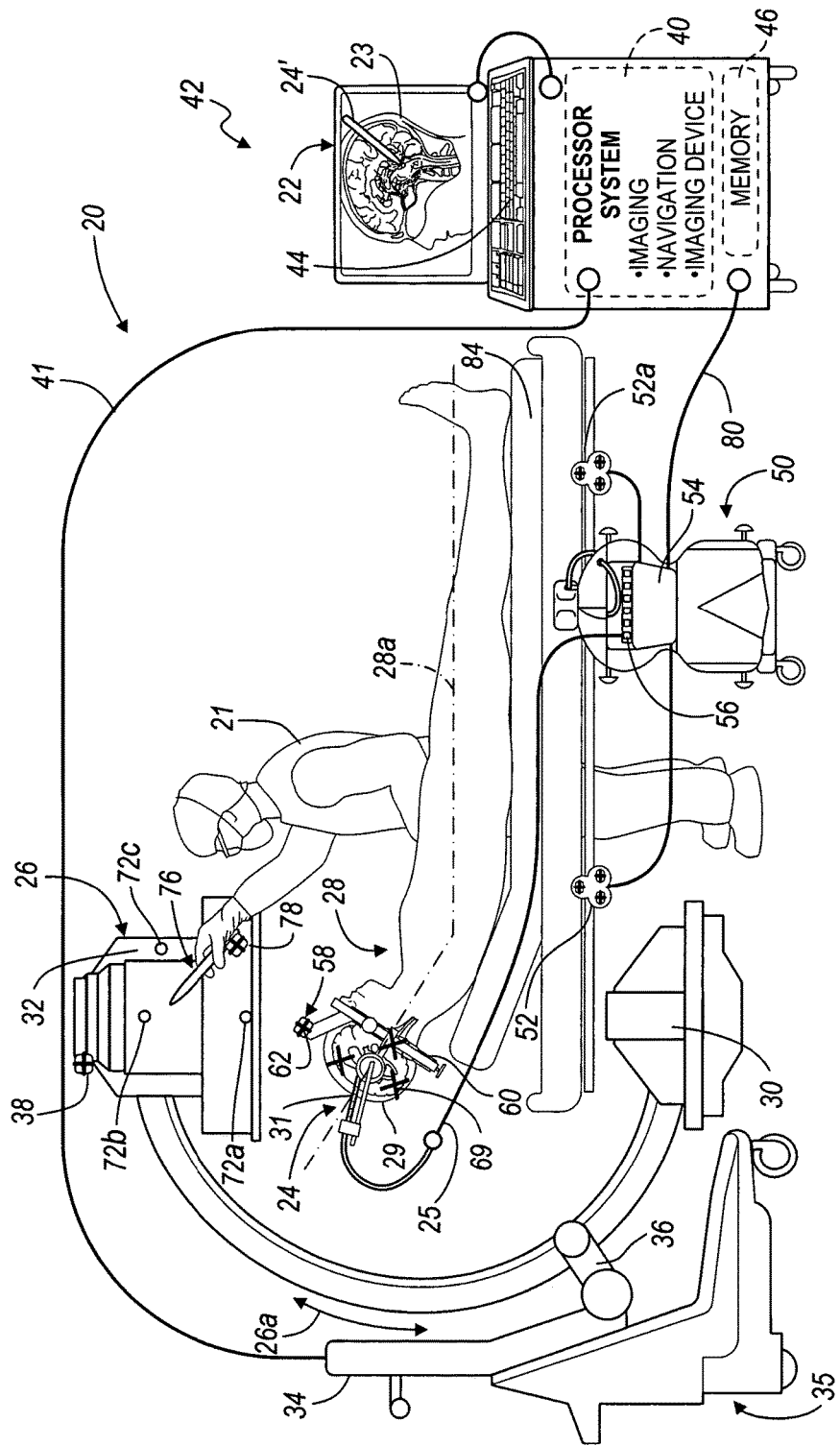
FIG. 1 is an environmental view of a surgical navigation system according to various embodiments.

A guided procedure can be performed with a navigation system 20, illustrated in FIG. 1. The guided procedure can be any appropriate procedure, such as a neural procedure, a cardiac procedure, spinal procedure, and orthopedic procedure. The navigation system 20 can include various components, as will be discussed further herein. The navigation system 20 can allow a user, such as a surgeon 21 to view on a display device 22 a relative position of an instrument 24 to a coordinate system. The coordinate system can be relative to image data displayed on the display device 22, to a patient only, to a point outside of a patient, or combinations of these. Further, the system can be used with image data, imageless, atlas data, or combinations of these.

It should further be noted that the navigation system 20 can be used to navigate or track various instruments including: catheters, probes, needles, guidewires, instruments, implants, deep brain stimulators, electrical leads, etc. Moreover, the instrument 24 can be used in any region of the body. The navigation system 20 and the instrument 24 can be used in any appropriate procedure, such as one that is generally minimally invasive, arthroscopic, percutaneous, stereotactic, or an open procedure.

Also, the single illustrated instrument 24 is only exemplary of any appropriate instrument and may also represent many instruments, such as a series or group of instruments. Identity and other information relating to the instrument 24 can also be provided to the navigation system 20. Information from an instrument tracking device 31 can be transmitted along an information system 25 to the workstation. Further, the information about the instrument 24 can also be displayed on the display device 22 for viewing by the surgeon 21.

The navigation system 20 can include an imaging device 26 that is used to acquire pre-, intra-, or post-operative or real-time image data of a patient 28. The imaging device 26 can be, for example, a fluoroscopic x-ray imaging device that may be configured as, and also referred to as, a C-arm 26 having an x-ray source 30 and an x-ray receiving section 32. The sections can be mounted relative to one another and moveable relative to a base 35. The base 35 can be fixed relative to the patient 28. An optional calibration and tracking target and optional radiation sensors can be provided, as understood by one skilled in the art. An example of a fluoroscopic C-arm x-ray device that may be used as the imaging device 26 is the ARCADIS® Orbic or ARCADIS® Orbic 3D from Siemens Medical of Germany. Other exemplary fluoroscopes include bi-plane fluoroscopic systems, ceiling fluoroscopic systems, cath-lab fluoroscopic systems, fixed C-arm fluoroscopic systems, 3D fluoroscopic systems, O-arm™ imaging devices (i.e. devices sold by Breakaway Imaging, LLC. having a place of business in Massachusetts, USA), etc.

An optional imaging device controller 34 can control the imaging device 26 to capture the x-ray images received at the receiving section 32 and store the images for later use. The receiving section 32 can also be referred to as or act as, according to various embodiments, an image collection section or image intensifier. The controller 34 may also be separate from the C-arm 26 or located a distance from the C-arm 26. The controller 34 can control the C-arm 26 to control movement in the direction of arrow 26a or rotate about a longitudinal axis 28a of the patient 28, allowing anterior or lateral views of the patient 28 to be imaged. Each of these movements involves rotation about a mechanical axis 36 of the C-arm 26.

The operation of the C-arm 26 is understood by one skilled in the art. Briefly, x-rays can be emitted from an x-ray section 30 and received at a receiving section 32. The receiving section 32 can include a camera that can create the image data from the received x-rays. Further, a C-arm tracking device 38 can be provided to track a position of any portion of the C-arm 26, such as the receiving section 32, at any appropriate time by the tracking system 50.

It will be understood that image data can be created or captured with any appropriate imaging device, such as a magnetic resonance imaging system, a positron emission tomography system, computed tomography, an ultrasound system, or any appropriate system. It will be further understood that various imaging systems can be calibrated according to various known techniques. The use of the C-arm 26, however, can be used according to various embodiments disclosed herein.

The image data can be forwarded from the C-arm controller 34 to a navigation computer and/or processor system 40 via a communication system 41. The communication system 41 can be wireless, wired, a data transfer device (e.g. a CD-Rom or DVD-Rom), or any appropriate system. The processor system 40 can also include the C-arm controller 34. The C-arm controller 34 and the processor system 40 can also, therefore, include a BUS communication system or internal communication. It will also be understood that the image data is not necessarily first retained in the controller 34, but may be directly transmitted to a workstation 42 or to a tracking system 50, as discussed herein.

A work station 42 can include the processor system 40, the display device 22, a user interface 44, and a memory 46. The processor system 40 can process the image data, navigation data, etc. The processor system 40 can include one or more separate processors.

The work station 42 provides facilities for displaying the image data 23 as an image on the display device 22, saving, digitally manipulating, or printing a hard copy image of the received image data 23. The user interface 44 may be a keyboard, mouse, touch pen, touch screen or other suitable device. The user interface device 44 allows a physician or user to provide inputs to control the imaging device 26, via the C-arm controller 34, or adjust the display settings of the display device 22. The user interface 44 can also allow a user to manipulate the navigation system 20 in any selected manner.

While the imaging device 26 is shown in FIG. 1, any other alternative 2D, 3D or 4D imaging modality may also be used. As disclosed herein any appropriate imaging system can be used in the navigation system to provide image data. The imaging system 26 can generally provide information regarding movement of a capturing or receiving section 32 thereof to determine a position of the capturing portion relative to the patient 28. For example, any 2D, 3D or 4D imaging device, such as isocentric fluoroscopy, three-dimensional (3-D) fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative CT, single photo emission computed tomography (SPECT), or planar gamma scintigraphy (PGS) may also be used to acquire 2D, 3D or 4D pre- or post-operative and/or real-time images or image data of the patient 28. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, can also provide functional image data superimposed onto anatomical data to be used to confidently reach target sites within the patient 28. It should further be noted that the optional imaging device 26, as shown in FIG. 1, provides a virtual bi-plane image using a single-head C-arm fluoroscope as the optional imaging device 26 by simply rotating the C-arm 26 about at least two planes, which could be orthogonal planes to generate two-dimensional images that can be converted to three-dimensional volumetric images. By acquiring images in more than one plane, an icon representing the location of an impacter, stylet, reamer driver, taps, drill, deep brain stimulators, electrical leads, needles, implants, probes, or other instrument, introduced and advanced in the patient 28, may be superimposed in more than one view on the display device 22 allowing simulated bi-plane or even multi-plane views, including two and three-dimensional views.

With continuing reference to FIG. 1, the navigation system 20 can further include the electromagnetic (EM) tracking system 50 that includes a localizer 52 (e.g. a coil array or multiple coil arrays), a coil array controller 54, a navigation interface 56 for an instrument tracking device, and a dynamic reference frame 58. The dynamic reference frame can be used to determine at any point in time a position of the patient 28 in the navigated space.

The dynamic reference frame 58 can include a dynamic reference frame member or holder 60 and a removable tracking device 62. Alternatively, the dynamic reference frame 58 can include a tracking device that is formed integrally with the dynamic reference frame member 60. One skilled in the art will understand that the tracking device 62 can be any appropriate device that can be an emitter, a receiver, a reflector, a sensor to sense a field, or any other appropriate device that can be tracked by a tracking system including the localizer 52.

The localizer coil array 52 may also be supplemented or replaced with a second localizer 52*a*. The second localizer 52*a* may be the same as the first localizer 52 or different, such as that described in U.S. patent application Ser. No. 10/941,782, filed Sep. 15, 2004, now U.S. Pat. App. Pub. No. 2005/0085720, and entitled "METHOD AND APPARATUS FOR SURGICAL NAVIGATION", herein incorporated by reference.

As is understood the localizer array 52 can transmit signals that are received by an appropriate tracking device. The signal transmitted by the localizer 52 can be an electromagnetic field that will have a different strength at any position in the field. The coil array 52 can include a plurality of coils each operable to generate distinct electromagnetic fields into the navigation region of the patient 28, which is sometimes referred to as patient space. Electromagnetic systems are generally described in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The tracking device, such as the dynamic reference frame 58, an instrument tracking device 31 on the instrument 24, the tracking device 38 on the imaging device 26, etc can sense the field strength at their respective locations. The dynamic reference frame 58, the instrument tracking device 31, the tracking device 38 can then transmit signals based upon the received signals from the array 52, 52*a*. One skilled in the art will also understand that the localizer 52, 52*a* can receive or sense a field produced by the various tracking devices 62, 31, 38 as well. Thus the system can work in either manner or a combination.

It should further be noted that the entire tracking system 50 or parts of the tracking system 50 may be incorporated into the imaging device 26. For example, one of the localizers can be incorporated into the imaging device 26. Incorporating the tracking system 50 may provide an integrated imaging and tracking system. Any combination of these components may also be incorporated into the imaging system 26, which can include any appropriate imaging device.

The coil array 52 can be positioned at any appropriate location. For example it can be attached to the receiving section 32 of the C-arm 26. Alternatively, the coil array 52 may be positioned at the x-ray source 30, within or atop an operating room (OR) table 84, on siderails associated with the OR table 84, or positioned on the patient 28. The coil array 52 may also be positioned in the items being navigated.

The coil array 52 is controlled or driven by the coil array controller 54. The coil array controller 54 can drive each coil in the coil array 52 in a time division multiplex or a frequency division multiplex manner. In this regard, each coil may be driven separately at a distinct time or all of the coils may be driven simultaneously with each being driven by a different frequency, as discussed further herein. This arrangement makes the coil array 52 a transmitter coil array. It will be understood that the coil array may also receive, as discussed above. Thus, reference to a transmitter coil array is merely exemplary and not intended to limit the type of localizer used in a selected tracking system.

Upon driving the coils in the transmitter coil array 52 with the coil array controller 54, electromagnetic fields are generated within the patient 28, which is sometimes referred to as patient space. The electromagnetic fields generated in the patient space induce currents in the tracking devices 38, 62, 31 positioned in the navigation field. These induced signals are delivered to the navigation device interface 56 and can be forwarded to the coil array controller 54, as discussed above. Again, it will be understood that the tracking devices may transmit a field and induce a signal in the localizer 52.

The navigation device interface 54 may provide all the necessary electrical isolation for the navigation system 20, as discussed herein. The navigation device interface 56 can also include amplifiers, filters and buffers to directly interface with the tracking devices 62, 31 in the instrument 24. Alternatively, the tracking devices 38, 62, 31, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled with a physical cord to the navigation device interface 56.

When the navigation system 20 uses an EM based tracking system, various portions of the navigation system 20, are equipped with at least one, generally multiple coils. The coils can be used with the EM localizer arrays 52, 52*a* to determine a position of the coils. The coils are generally defined by tracking devices 31, 38, 62 that are associated with the portions to be tracked. Thus, determining a position of the coils allows a determination of a position of the tracking devices and the portions to which they are attached. Alternatively, the tracking system 50 may be a hybrid system that includes components from various tracking systems such as optical, acoustic, radiation, radar, etc.

The tracking device 31 on the instrument 24 can be in a handle or inserter that interconnects with an attachment portion. The instrument may be or may assist in placing an implant or in driving a selected portion. The instrument 24 can include a graspable or manipulable portion at a proximal end at the tracking device and can be fixed near the manipulable portion of the instrument 24 or at a distal working end. The tracking device 24 can include an electromagnetic sensor to sense the electromagnetic field generated by the transmitter coil array 52 that can induce a current in the tracking device 31, or vice versa as discussed above.

The dynamic reference frame 58 of the tracking system 50 can also be coupled to the navigation device interface 56 to forward the information to the coil array controller 54. The dynamic reference frame 58, according to various embodiments, may include a small magnetic field detector as the tracking device 62. The dynamic reference frame 58 may be fixed to the patient 28 adjacent to the region being navigated so that any movement of the patient 28 is detected as relative motion between the transmitter coil array 52 and the dynamic reference frame 58. The dynamic reference frame 58 can be interconnected with the patient 28 in any appropriate manner, including those discussed herein. Any relative motion is forwarded to the coil array controller 54, which updates registration correlation and maintains accurate navigation, further discussed herein. An electromagnetic dynamic reference frame 58 can be configured as a pair or trio of orthogonally oriented coils, each having the same center or may be configured in any other non-coaxial or co-axial coil configurations.

The dynamic reference frame 58 may be affixed externally to the patient 28, adjacent to the region of navigation, such as on the patient's cranium, etc., as shown in FIG. 1. The dynamic reference frame 58 can be affixed to the patient's skin, by way of a selected adhesive patch and/or a tensioning system. The dynamic reference frame 58 may also be removably attachable to a fiducial marker 69. The fiducial markers can be anatomical landmarks or members attached or positioned on the patient's 28 body. The dynamic reference frame 58 can also be connected to a bone portion of the anatomy. The bone portion can be adjacent the area of the procedure, the bone of the procedure, or any appropriate body portion.

Although the discussion above is directed to an electromagnetic navigation and tracking system, it will be understood that any appropriate tracking system can be used as the tracking system 50. For example, one skilled in the art will understand that appropriate tracking systems include, but are not limited to, an optical tracking system, a radar tracking system, an acoustic tracking system, an accelerometer tracking system. Nevertheless, the tracking system can include any appropriate portions such as an appropriate localizer for the tracking system and appropriate tracking devices for the tracking system. Thus, the discussion herein regarding an electromagnetic tracking system is merely exemplary of any appropriate tracking system. Also, more than one tracking system can be used during a procedure, such as a hybrid system discussed above. Thus, an EM and an optical tracking system can be used at the same time to track a tracking device within the same space.

Briefly, the navigation system 20 operates as follows. The navigation system 20 creates a translation map between all points in the image data or image space and the corresponding points in the patient's anatomy in patient space. After this map is established, the image space and patient space are registered. In other words, registration is the process of determining how to correlate a position in image space with a corresponding point in real or patient space. This can also be used to illustrate a position of the instrument 24 relative to the proposed trajectory and/or the determined anatomical target. The work station 42 in combination with the coil array controller 54 and the C-arm controller 34 identify the corresponding point on the pre-acquired image or atlas model relative to the tracked instrument 24 and display the position on display device 22 and relative to the image data 23. This identification is known as navigation or localization. An icon representing the localized point or instruments is shown on the display device 22 within several two-dimensional image planes, as well as on three and four dimensional images and models.

To register the patient 28, the surgeon 21 may use point registration by selecting and storing particular points from the pre-acquired images and then touching the corresponding points on the patient's 28 anatomy with a pointer probe or any appropriate tracked device, such as the instrument 24. The navigation system 20 analyzes the relationship between the two sets of points that are selected and computes a match, which allows for a determination of a correlation of every point in the image data or image space with its corresponding point on the patient's anatomy or the patient space.

The points that are selected to perform registration or form a translation map are the fiducial markers 69, such as anatomical or artificial landmarks. Again, the fiducial markers 69 are identifiable on the images and identifiable and accessible on the patient 28. The fiducial markers 69 can be artificial landmarks that are positioned on the patient 28 or anatomical landmarks that can be easily identified in the image data. The artificial fiducial markers 69, can also form part of the dynamic reference frame 58, such as those disclosed in U.S. Pat. No. 6,381,485, entitled "Registration of Human Anatomy Integrated for Electromagnetic Localization," issued Apr. 30, 2002, herein incorporated by reference. It will be understood that the "X" illustrated in FIG. 1 can merely indicate a position of a fiducial marker 69 rather than being the fiducial marker 69.

The system 20 may also perform registration using anatomic surface information or path information as is known in the art (and may be referred to as auto-registration). The system 20 may also perform 2D to 3D registration by utilizing the acquired 2D images to register 3D volume images by use of contour algorithms, point algorithms or density comparison algorithms, as is known in the art. An exemplary 2D to 3D registration procedure is set forth in U.S. Ser. No. 10/644,680, filed on Aug. 20, 2003, now U.S. Pat. App. Pub. No. 2004-0215071, entitled "Method and Apparatus for Performing 2D to 3D Registration", incorporated herein by reference.

In order to maintain registration accuracy, the navigation system 20 can continuously track the position of the patient 28 during registration and navigation with the dynamic reference frame 58. This is because the patient 28, dynamic reference frame 58, and transmitter coil array 52 may all move during the procedure, even when this movement is not desired. Alternatively the patient 28 may be held immobile once the registration has occurred, such as with a head frame. Therefore, if the navigation system 20 did not track the position of the patient 28 or area of the anatomy, any patient movement after image acquisition would result in inaccurate navigation within that image. The dynamic reference frame 58 allows the tracking system 50 to track the anatomy and can assist in registration. Because the dynamic reference frame 58 is rigidly fixed to the patient 28, any movement of the anatomy or the transmitter coil array 52 is detected as the relative motion between the transmitter coil array 52 and the dynamic reference frame 58. This relative motion is communicated to the coil array controller 54, via the navigation probe interface 56, which updates the registration correlation to thereby maintain accurate navigation.

The dynamic reference frame 58 can be affixed to any appropriate portion of the patient 28, and can be used to register the patient space to the image data or image space, as discussed above. For example, when a procedure is being performed relative to a cranium 29, the dynamic reference frame 58 can be interconnected with the cranium 29. The dynamic reference frame 58 can be interconnected with the cranium 29 in any appropriate manner, such as those discussed herein according to various embodiments.

The navigation system 20 can detect both the position of the patient's anatomy and the position of the device 58 or attachment member (e.g. tracking device 31) attached to the instrument 24. Knowing the location of these two items allows the navigation system 20 to compute and display the position of the instrument 24 or any portion thereof in relation to the patient 28, after registration. The tracking system 50 is employed to track the instrument 24 and the anatomy 28 simultaneously, as discussed above according to various embodiments.

To obtain maximum accuracy it can be selected to fix the dynamic reference frame 58 in each of at least 6 degrees of freedom. Thus, the dynamic reference frame 58 or any of the tracking sensors 258 can be fixed relative to axial motion X, translational motion Y, rotational motion Z, yaw, pitch, and roll relative to the portion of the patient 28 to which it is attached. Any appropriate coordinate system can be used to describe the various degrees of freedom. Fixing the dynamic reference frame 58 relative to the patient 28 in this manner can assist in maintaining maximum accuracy of the navigation system 20.

The instrument 24 can be any appropriate instrument (e.g., a catheter, a probe, a guide, etc.) and can be used for various procedures and methods, such as delivering a material to a selected portion of the patient 28, such as within the cranium 29. Other exemplary instruments can also be implantable members, scissors, clamps, retractors, etc. The material can be any appropriate material such as a bioactive material, a pharmacological material, a contrast agent, or any appropriate material. As discussed further herein, the instrument 24 can be precisely positioned via the navigation system 20 and otherwise used to achieve a protocol for positioning the material relative to the patient 28 in any appropriate manner, such as within the cranium 29. The instrument 24 may also include a brain probe to perform deep brain stimulation.

The delivery of a material or the performing of an intervention or procedure in the anatomy can be assisted with images obtained by the imaging device 26. The imaging device 26 can obtain images of the patient 28 for display on the display device 22. The procedure can be assisted, such as with navigation, by displaying an icon 24' illustrating a position of the instrument 24 relative to the patient 28 on the display device 22 relative to the image data 23. This can assist the surgeon 21 in determining the position of the instrument 24 relative to the patient 28 and relative to a planned position of the instrument 24. The positioning of the instrument 24 relative to the patient 28, however, and its determination or navigation with the tracking system 50 can be enhanced by determining or knowing the position of the imaging device 26 relative to the patient 28 when the image data is captured.

According to various embodiments, the tracking device 38 associated with the imaging device 26 can be used to continuously track the position of the image intensifier 32. The navigation system 20 can display on the display device 22 the image data 23 and the icon 24' of the instrument 24. The navigation system can perform this task because the tracking system 50 can determine the position of the image intensifier 32, the position of the instrument 24, and the position of the patient 28. The tracking device 38 can be positioned at any appropriate location on the imaging device 26. Positioning the tracking device 38 near the image intensifier 32 can be selected because the determination of the image data is captured in the intensifier 32.

One skilled in the art will understand that the image obtained with the imaging device 26 can be dependent upon the position of the image intensifier 32 relative to the patient 28. For example, a true or absolute anterior to posterior view can require the positioning of the image intensifier directly on the plane or axis that defines an anterior to posterior axis through the patient 28. It may be difficult, however, to position the imaging device 26 at the exact anterior-to-posterior plane of the patient 28. Therefore, the tracking device 38 can assist in determining the position of the image intensifier 32 relative to the patient 28 and the instrument 24. Briefly, as discussed above, the position of the patient 28 can be determined with the dynamic reference frame 58 and the position of the instrument 24 can be determined with the tracking device 31.

In addition, or alternatively, the tracking device 38 positioned on the imaging device 26 can determine its position relative to the patient 28. The Imaging device processor can be a part of the C-arm controller 34, the processor system 40, or any appropriate portion. The imaging device processor can, in various embodiments, be integrated or separate from any processor portion. The imaging device processor can assist in determining the location of the imaging device 26, or any appropriate portion thereof, relative to the patient 28. It will be understood that the discussion of the image intensifier 32 can be understood to be the position of any appropriate portion of the imaging device 26. The discussion relating to only the position of the imaging intensifier 32 is merely for brevity and clarity of the current discussion.

The image intensifier 32 can be localized or located relative to the patient 28, the localizer 52, or any appropriate portion. It can be selected to determine the position of the image intensifier 32 relative to the patient 28. As discussed above the position of the patient 28 can be determined with the dynamic reference frame 58. The image intensifier can then be localized with a localization portion, such as one or more localization divots or points 72 (illustrated separately as 72a, 72b, and 72c.) The imaging device localization point 72 can be positioned anywhere on the imaging device 26. The localization point 72 are illustrated on selected positions of the image intensifier 32 merely for exemplary purposes. Further, any appropriate number of the imaging device localization points can be provided. For example, three image device localization points 72a, 72b, 72c can be used to determine a plane or position of the image intensifier 32. The determined position of the intensifier 32 can be relative to the patent 28, the localizers 52, 52a or any other appropriate portion. The imaging device localization point 72 can be touched with a localization or indication device 76.

The localization device 76 can be any appropriate device or instrument, such as a pointer or pointing probe which can include a tracking device 78. The tracking device 78 can be tracked with the tracking system 50 and the localization array 52, 52a, as discussed above. The tracking device 78 can be any appropriate tracking device, and can include three coils, or any appropriate number of coils, positioned relative to one another to be tracked with a tracking system 50.

The surgeon 21 can touch the imaging device localization points 72 with the localizing device 76. The tracking system 50 can track the tracking device 78 to determine the position of any points of the localization device 76. The information transferred of any position of the localization device 76 can be transferred on a communication system or line 80.

The navigation system 20 can then determine the position of the imaging intensifier 32 in the navigation space. As discussed above, the communication system 80 can transfer information from the tracking system 50 to the work station 42 and the processor system 40. Also, as discussed above, the processor system 40 can include a navigation portion to determine the position of the tracked portion, such as the localization instrument 76, relative to the imaging device 26. The navigation processor can be included in the tracking system. Alternatively, the tracking system 50 can also include a tracking processor separate from the navigation processor.

Once the appropriate portions of the image intensifier 32 have been touched with the localization device 76, the position of the image intensifier 32 can be determined. The position can be determined in any coordinate system, such as relative to a selected portion, such as to the patient 28. The determination or knowledge of the position of the image intensifier 32 relative to the patient 28 can then be used to assist in determining an appropriate position of the icon 24' displayed on the display device 22 relative to the image data 23.

Figure 2:
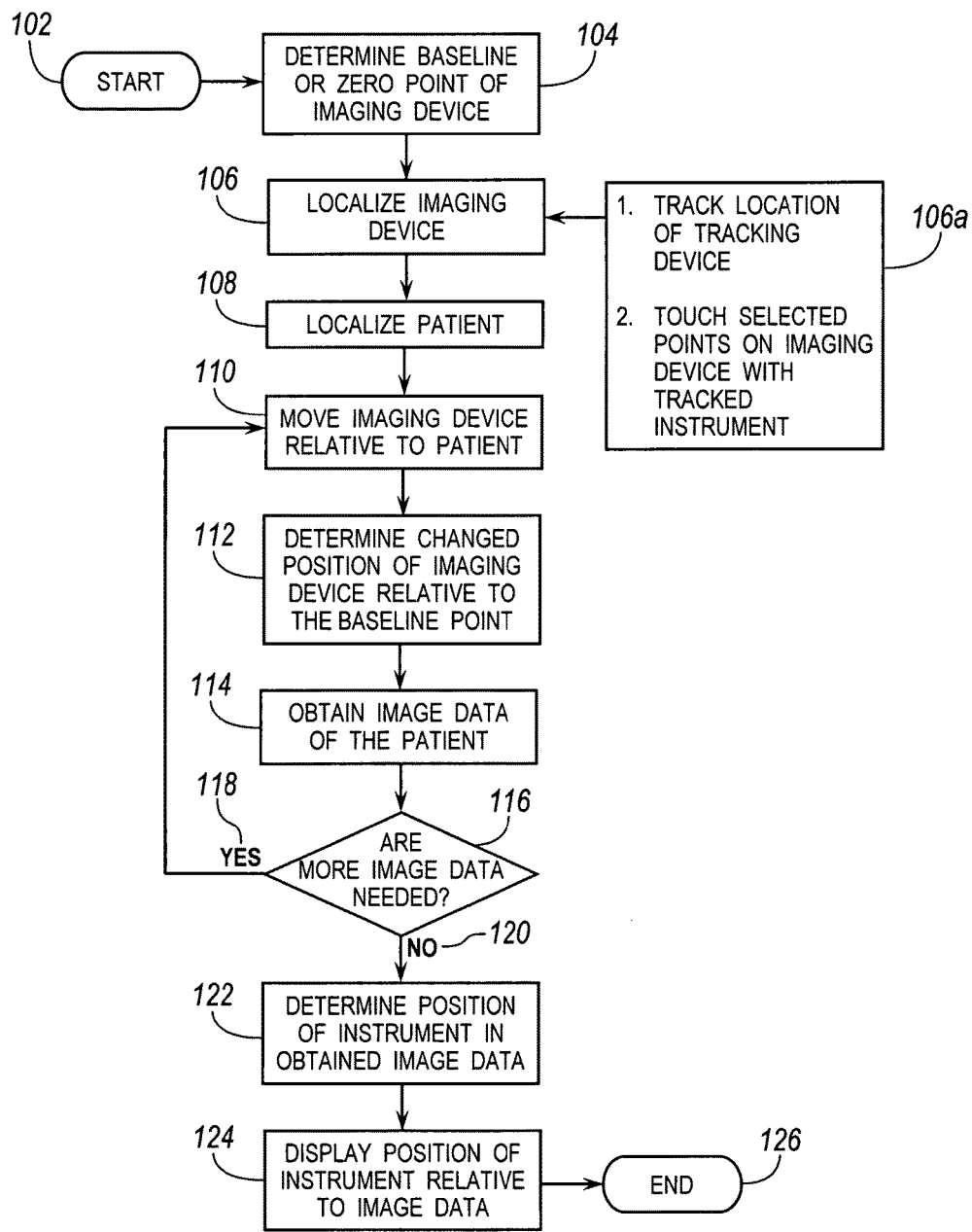
FIG. 2 is a flow chart illustrating a method according to various embodiments.

With reference to FIG. 2, a flow chart 100 is shown to illustrate a system for determining the position of the instrument 24 relative to the patient 28. The position of the instrument 24 can be displayed on the display device 22 as the icon 24' superimposed on the image data 23. As discussed above, the imaging device processor, which can be included in the controller 34, can determine or know the position of the image intensifier 32 relative to the base 35.

Also, as discussed above, the imaging device 26 can be moved relative to the patient 28. For example, the imaging device, and particular the image intensifier 32, can be rotated, tilted and moved in any direction relative to the patient 28. Therefore, movement of the imaging device 26 relative to the patient 28 can alter a perspective of the image data collected with the image intensifier 32 of the patient 28. Determining movement of the image intensifier 32, however, with the controller 34 (or as discussed above any appropriate portion and the use of the controller 34 herein is merely exemplary) can allow its location relative to the patient 28 can be determined.

Therefore, the method or process 100 can start in block 102. Then a determination of a baseline or zero point of the imaging device can be performed in block 104. The determination of the baseline point of the imaging device is generally performed with the imaging device processor, which can be provided at any appropriate portion of the navigation system 20. The baseline point of the imaging device 104 is provided, in most part, to determine a point relative to which a change of position of the imaging device 26 can be determined. Therefore, one skilled in the art will understand, the baseline point of the imaging device 26 can be arbitrary and can be any appropriate location of the imaging device 26.

The baseline point, as discussed further herein, can be acquired or determined at any appropriate time. For example, prior to a first set or first image data acquisition of the patient 28, a baseline can be determined. The baseline point can be determined by touching points on the imaging device 26, as discussed further herein, the controller 34, or any other appropriate system. For example, the imaging device 26 can include a three dimensional imaging system, therefore the determination of the position of the imaging device can be based upon the image data acquired of the patient 28.

The baseline can be used to determine the position of the imaging device 26 at a first point and time and can be compared to a position of the imaging device at a second point and time. For example, the baseline can include a determined position of the imaging device prior to image acquisition, during image acquisition, or subsequent to image acquisition of the patient 28. In addition, baseline point can include the determination of a point of the imaging device substantially immediately prior to image acquisition and a second point determination can be determine substantially immediately after image acquisition. The two points can then be compared to determine whether the imaging device 26 or the patient 28 moved during image acquisition. As discussed further herein, various techniques can be used to determine the baseline point, such as with the controller, a touch probe, or other appropriate technique.

Once the determination of the baseline point of the imaging device has been determined in block 104, the imaging device can be localized in block 106. The localization of the imaging device 26 can be performed in any appropriate manner, including those discussed above. For example, the tracking device 38 can be tracked with the tracking system 50. Alternatively, or in addition thereto, a position of the imaging device localization points 72 can be determined with a tracking system 50. For example, the localization points 72 can be touched with the localization device 76. It will be understood that any other appropriate system can also be used to localize the image device in block 106 as illustrated in block 106a.

The determined baseline point in block 104 can be defined or redefined as the localized position of the imaging device in block 106. For example, an arbitrary location of the imaging device 26 can be determined in block 104 as the baseline point. The baseline point can then be transferred or correlated to the localized position of the imaging device performed in block 106. The determination in block 104 at any appropriate time, however, is merely arbitrary and not required. The localization in block 106 defines a position of the imaging device in the navigation or patient space of the navigation system 20.

After the imaging device has been localized, substantially concurrently therewith, or at any appropriate time, the patient can also be localized in block 108. The localization of the patient in block 108 can be performed in any appropriate manner, including those discussed above. For example, the dynamic reference frame 58 can be tracked with the tracking device 50. Further, the position of the dynamic reference frame 58, and the patient relative thereto 28, can be determined substantially at the same time with a localization of the imaging device 26. Localizing the patient 28 and the imaging device 26 can ensure that the position of the patient 28 relative to the imaging device 26 is known at any appropriate time, such as at the baseline or zero point time.

The imaging device can then be moved in block 110. The movement of the imaging device 26 in block 110 can be performed for any appropriate reason. For example, the surgeon 21 may select to obtain an appropriate initial image or multiple images of the patient 28. These can include an anterior-to-posterior view, a medial-to-lateral view, or any other appropriate view of the patient 28. Obtaining various images of the patient 28 can be performed by moving the imaging device 26 relative to the patient 28 to obtain different views.

The movement of the imaging device in block 110 can be determined substantially precisely. The movement of the imaging device can generally be determined within an acceptable error for the navigation or procedure system. For example, the position of the imaging device can be determined to an error of about one millimeter, according to various embodiments. This error can be acceptable for selected procedures. It will be understood, however, that the movement or position of the imaging device can be determined to an error of zero millimeters to about two centimeters. According to various embodiments, the acceptable error can be about one centimeter to about two centimeters.

After moving the imaging device 26 from the baseline point, determined in block 104, a determination of a change in position of the imaging device 26 relative to the zero point can be made in block 112. The change in the position can be any appropriate change. For example, a rotational change can occur, a tilt change can occur, a yaw change can occur, or any other appropriate change. Nevertheless, the change in the position of the imaging device 26 relative to the baseline point determined in block 104 can be determined with the imaging device processor, such as the controller 34. The change in position can be determined based upon movements, such as with a mechanical portion of the imaging device 26. The movement can be any appropriate movement. The movement can generally be regulated or determined with the imaging device processor.

Image data can then be obtained in block 114 of the patient 28. The determination of the change in position of the imaging device, determined in block 112, can assist in determining the appropriate perspective or orientation of the image data, obtained in block 114, relative to the patient 28. The image data obtained in block 114 can be displayed relative to or compared to image data also obtained at any other appropriate time, such as at the baseline position or at any other position relative to the patient. Therefore, it will be understood that multiple images can be obtained of the patient 28 by obtaining multiple images at many selected locations or moving the imaging device.

Whether more image data is required can be determined in block 116. If the determination or answer is Yes, then YES path 118 can be followed to move the imaging device in block 110, determine the change in position relative to the zero in block 112, and obtaining image data in block 114. Therefore, any appropriate number of image data can be obtained. Also, the change in position of the imaging device can be determined each time, relative to the baseline point can be made in block 104.

The determination of the position of the imaging device 26 can be determined during any portion of the image acquisition of the patient 28. In addition, the image data acquired of the patient 28 can also be used to determine movement of the patient 28 during the acquisition of the image data. The patient 28, who may move during or subsequent to image acquisition, can be determined such as with the dynamic reference frame 58 and determining its position relative to the baseline point of the imaging device 26. Therefore, the position of the patient 28 can be determined relative to the baseline point of the imaging device 26, as can the position of the imaging device 26 relative to the baseline position or point.

As discussed further herein, the position of the image data or its orientation for display on the display device 22 can be appropriately oriented relative to the movement of the patient 28 or the imaging device 26. In determining the movement of the imaging device 26 or the patient 28, the orientation of the instruments 24 relative to the image data 23 on the display device 22 can be provided. The orientation can be based upon the determined movement of the patient or the imaging device 26.

If the determination is NO at line 120, then a determination of a position of the instrument in the obtained image data can be made in block 122. Again, the orientation of the patient 28, as illustrated in the image data obtained with imaging device 26, can depend or be based in part upon the orientation of the imaging device 26 relative to the patient 28. Further, the position of the instrument 24 relative to the patient 28, as displayed on the display device 22 with the icon 24' can also depend, at least in part, on the orientation of the imaging device relative to the patient 28.

As one skilled in the art will understand the imaging device 26, which can be a C-arm, only takes substantially two dimensional images along an axis from the emitter portion to the image intensifier 32. A perspective or orientation of the image intensifier 32 relative to the patient 28 can determine or alter the perspective of various portions relative to the patient 28. Therefore, knowing a perspective or orientation of how the image data was obtained can assist or determine a position of the instrument 24 relative to the image data 23. Also, a 3-D fluoroscopy system can create a 3-D display based on multiple images. Thus, determining the relative orientation of the patient 23 and the imaging device 26, during the acquisition of each image data set, can ensure appropriate 3-D rendering of the image data.

Once the image data has been obtained and the position of the instrument has been determined, the position of the instrument relative to the image data can be displayed in block 124 on the display device 22. The process can then end in block 126. The icon 24' can be displayed on the display device 22 for viewing by the surgeon 21 with the determination of the position of the instrument 24. This can assist the surgeon 21 in performing a procedure on the patient 28.

With additional reference to FIGS. 3A-3C, the method 100 will be exemplary illustrated. The imaging device 26 can be positioned relative to the patient 28 and the baseline point can be determined for the imaging device 26, as discussed in block 104. The imaging device 26 can then be localized, as in block 106, and the patient 28 can be localized as in block 108. The imaging device 26 can also be registered to the patient 28 at this time. For example, the position of the imaging device 26 at the baseline point can be compared to the position of the patient 28 at the same time, thus registering the two. This registration can also be used to determine the position of the imaging device 26 relative to the patient at any appropriate time.

The display device 22 can display any appropriate image data, such as image data 23a obtained when the imaging device is at the baseline point or position. The display device 22 can also include a legend 130 that can include information of the position of the imaging device 26 relative to the patient 28. For example, the baseline point determined in block 104 can be displayed as zero, such as a zero degree rotation and zero degree tilt. Therefore, the baseline image data can be that illustrated in FIG. 3A.

The imaging device 26 can then be moved relative to the patient 28, as illustrated in FIG. 3B and discussed in block 110. The determined position of the imaging device 26 or change thereof relative to the baseline point can also be made, such as in block 112, and displayed on the legend 130. Image data can also then be obtained at the changed position, as in block 114, and illustrated on the display device 22 as image data 23b. The position of the instrument 24 relative to the patient 28 can be displayed on the display 22 relative to the image data 23b as an icon 24'b. The position of the icon 24'*b* relative to the image data 23*b* can be based upon the determined position of the imaging device 26, and the determined position of the instrument in block 122. The display on the display device 22 can follow the determinations as discussed in block 124.

Additional image data can be obtained by the surgeon 21, as illustrated in FIG. 3C. The determination in block 116 can be Yes to follow path 118 to again move the imaging device, such as in block 110, determine a change in position of the imaging device relative to the baseline point, such as in block 112, and obtain further image data 23*c*, as in block 114. Again, the determination of the position of the instrument 24 can be performed in block 122 and displayed on the display device 22, as discussed in block 124, as an icon 24'*c*. The icon 24'*c* illustrates a position of the instrument 24 relative to the patient 28 for display on the image data 23*c*. The position of the icon 24'*c* can be based upon the determined position of the instrument 24 relative to the patient 28. The position of the instrument 24 can be based on the determined position of the imaging device 26 or movement of the imaging device 26.

Therefore, one skilled in the art will understand that the position of the imaging device 26 can be used to determine the position of the instrument 24 relative to the patient 28. The determined position of the instrument 24 can then be displayed on the display device 22 relative to image data 23. As discussed above the image data 23 displayed on the display 22 can be, in part, dependant upon the position of the imaging device 26 relative to the patient 28. Thus, determining the position of the imaging device 26 relative to the patient 28 can assist in determining the orientation or direction at which the image data is collected.

The position of the imaging device 26 can be determined based upon movement of the imaging device and can be made with a controller 34. The controller 34 can include an imaging device processor. The imaging device processor can determine the amount of movement or type of movement of the imaging device 26 relative to the determined baseline point. Therefore, the navigation system 20 can determine a position of the image intensifier 32 relative to the baseline point, determined in block 104. The determined position of the imaging device 26, or portion thereof, can be used to assist in determining an appropriate display of the icon 24' to represent the instrument 24 relative to the patient 28 on the display device 22.

The system, for example 100, can also remove the need of continuously tracking the imaging device 26. This can remove possible EM interference with the tracked position of the imaging device 26. It can also allow any imaging device to be used as it does not require a tracking device. Any appropriate points can be used as the localization points 72. The navigation system can determine a plane of the imaging device and the imaging processor can determine movement relative to the baseline point.

The teachings herein are merely exemplary in nature and, thus, variations that do not depart from the gist of the teachings are intended to be within the scope of the teachings. Such variations are not to be regarded as a departure from the spirit and scope of the teachings.

What is claimed is:

1. A navigation system to navigate a procedure relative to an anatomy, comprising:
   an imaging device;
   an imaging device processor, in communication with the imaging device, configured to determine a single baseline position of the imaging device at a first time and a current position of the imaging device relative to the baseline position at a second time later than the first time, wherein the current position is selected from a plurality of subsequent positions that are determined after the baseline position;
   a tracking system;
   an instrument configured to be tracked with the tracking system relative to the anatomy;
   a navigation processor, in communication with the tracking system, configured to determine the position of the instrument relative to the anatomy and generate an icon of the instrument at a selected perspective relative to at least one of a first image data acquired with the imaging system at the baseline position or a second image data acquired with the imaging system at the current position, wherein the generated icon matches a perspective of the instrument relative to the subject based at least on an orientation of the imaging device relative to the anatomy at the current position determined at least in part by a comparison between the determined baseline position and the determined current position of the imaging device; and
   a display device configured to display an image based on at least one of the first image data or the second image data and the icon representing the instrument at the selected perspective relative to the displayed image on the display device based at least in part on the determined baseline position or determined current position of the imaging device;
   wherein the icon is displayed on the display device relative to the image corresponding to the position of the instrument relative to the anatomy and the selected perspective based at least on the current position of the imaging device;
   wherein the navigation processor is configured to:
      determine the baseline position of the imaging device relative to the anatomy based upon the image device processor determination of the baseline position and the determined position of the imaging device relative to the anatomy during a collection of the first image data at the first time, and
      determine an orientation of the second image data relative to the anatomy based upon the determination of the current position of the imaging device with the imaging device processor during the acquisition of the second image data at the current position and the position of the anatomy;
   wherein the determined position of the instrument relative to the anatomy as displayed with the display device is determined at least in part based upon both the determined current position of the imaging device and the tracked position of the instrument.

2. The system of claim 1 wherein the imaging device includes an image collection section and a base;
   wherein the image collection section can move relative to the base while the base remains positioned relative to the anatomy.

3. The system of claim 2, wherein the imaging device processor is a separate processor from the navigation processor and is configured to determine the baseline position and the current position relative to the baseline position of the image collection section relative to the base.

4. The system of claim 2, wherein the tracking system is operably connected to the imaging device to determine a position of the imaging device relative to the anatomy.

5. The system of claim 4, wherein the tracking system includes a localization point defined on the imaging device and a localization device moveable relative to the localization point to be tracked by the tracking system;
  wherein a position of the localization point can be determined with the navigation processor by tracking the localization device that is moved relative to the localization point.

6. The system of claim 5, wherein the tracking system includes an electromagnetic tracking system and the localization device includes a tracking device trackable with the electromagnetic tracking system.

7. The system of claim 5, wherein the localization point defined on the imaging device includes a localization portion operably connected to the imaging device tracked only prior, subsequent, or combinations thereof to acquiring image data of the anatomy.

8. A navigation system to navigate a procedure to be performed in an anatomy, comprising:
  an imaging system including:
    an image collection portion;
    a mounting member, wherein the image collection portion is moveable with the mounting member between a first position and a plurality of second positions different from the first position;
    a position selection portion processor, in communication with the imaging system, to determine (i) the first position of the image collection portion and (ii) a change to the plurality of second positions of the image collection portion and (iii) communicate a signal regarding the change, wherein the change is related to movement of the image collection portion determined with the position selection portion processor;
    wherein a first image data is obtained at the first position and a second image data is obtained at each of the plurality of second positions;
  a tracking system including:
    a localization system;
    a localization device tracked with the localization system;
  an instrument tracked with the tracking system relative to the anatomy; and
  a navigation processor in communication with the localization system to determine a position of the instrument relative to the anatomy and the image collection portion at both the first position and the plurality of second positions and determine a perspective of a representation of the instrument relative to the first image data or the second image data based at least in part upon the tracked position of the instrument and the communication signal of the determined change of position of the image collection portion from the position selection portion processor.

9. The navigation system of claim 8, wherein the localization device includes at least one of a tracking member, a trackable instrument, a localization point, or combinations thereof.

10. The navigation system of claim 8, wherein the localization device includes a plurality of localization points defined on the image collection portion;
  a localization instrument configured to be tracked;
  wherein the tracking system is configured to track the localization instrument relative to the localization points; and
  wherein the navigation processor is configured to determine the position of the image collection portion based upon the tracked localization instrument to determine the position of the image collection portion relative to the anatomy.

11. The navigation system of claim 10, wherein the localization instrument includes an electromagnetic tracking device.

12. The navigation system of claim 8, wherein the imaging system includes at least one of an x-ray imaging system, isocentric fluoroscopy, three-dimensional (3-D) fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative CT, single photo emission computed tomography (SPECT), planar gamma scintigraphy (PGS), or combinations thereof.

13. The navigation system of claim 8, wherein the imaging system further includes a base positioned relative to the anatomy;
  wherein the mounting member is operable to move the image collection portion relative to the base between the first position and the second position.

14. The navigation system of claim 8, wherein the mounting member is configured to move the image collection portion relative to the anatomy.

15. The navigation system of claim 14, wherein the navigation processor is configured to determine the position of the instrument relative to the patient and further determine the position of the instrument relative to the first image data and the second image data collected with the imaging system.

16. The navigation system of claim 15, further comprising:
  a display device configured to display the image data and an icon representing a position of the instrument superimposed on the image data relative to the patient.

17. A method of performing a navigated procedure on an anatomy with an instrument, comprising:
  positioning an imaging device relative to the anatomy;
  determining a single baseline position of the imaging device with an imaging device processor during which a first image data is obtained and registering the imaging device to the anatomy at the baseline position of the imaging device;
  moving the imaging device relative to the anatomy to a plurality of second positions different from the baseline position;
  determining a change in position relative to the baseline position of the imaging device relative to the anatomy after moving the imaging device to the plurality of second positions relative to the anatomy;
  tracking an instrument relative to the anatomy;
  obtaining second image data of the anatomy when the imaging device is at the plurality of second positions;
  comparing the obtained second image data to the first image data;
  determining a position of the instrument relative to the obtained second image data, wherein the obtained second image data is from a selected perspective based at least in part on the determined change in position of the imaging device after moving the imaging device to at least each of the plurality of second positions and comparing the obtained second image data to the first image data; and displaying the determined position of the instrument as an icon superimposed on the obtained second image data;
wherein determining the position of the instrument is based on the determined change in position of the imaging device from the determined single baseline position to the selected plurality of second positions.

18. The method of claim 17, wherein determining the baseline position of the imaging device includes:
tracking a localization device moveable relative to localization points on the imaging device with an electromagnetic tracking system.

19. The method of claim 18, wherein tracking a localization device relative to the imaging device occurs only prior to, subsequent to, or combinations thereof to the obtaining image data of the anatomy.

20. The method of claim 17, further comprising:
providing an imaging device including at least one of an x-ray imaging device, isocentric fluoroscopy, three-dimensional (3-D) fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative CT, single photo emission computed tomography (SPECT), or planar gamma scintigraphy (PGS), or combinations thereof.

21. The method of claim 17, wherein determining the baseline position includes determining a position of an image collection portion of an imaging device relative to a base; and positioning the base relative to the anatomy wherein moving the imaging device includes maintaining the base in the position relative to the anatomy.

22. The method of claim 21, wherein determining a change in position of the imaging device includes providing the imaging device to include the imaging collection portion and the base and mounting assembly system;
wherein the mounting assembly system is configured to move the imaging collection portion relative to the base portion; and
wherein the imaging device processor is configured with the movement portion to determine the change in position of the imaging device.

23. The method of claim 22, wherein determining the position of the instrument includes determining the perspective of the first or second image data based upon the movement of the imaging device imaging collection portion with the mounting assembly system.

24. The method of claim 17, further comprising:
determining the baseline position of the imaging device relative to the anatomy by localizing an imaging collection portion of the imaging device;
obtaining third image data at a third position in addition to at least one of the plurality of second positions;
displaying the image based on at least one of the baseline position, at least one of the plurality of second positions, or the third position;

determining a position of the imaging device including a change from and relative to the baseline position at the third position;
determining a perspective of the instrument based upon the determined position of the imaging device and change from the baseline position to the third position; and
displaying a new icon representing the instrument super imposed on the third image data on a display based upon the determined perspective.

25. The method of claim 17, further comprising:
providing the imaging device to include an x-ray imaging device having an image receiving section; and
moving the imaging receiving section relative to the anatomy.

26. A navigation system to navigate a procedure relative to an anatomy, comprising:
a localization instrument that is tracked with a tracking system;
an imaging device having a device localization point, wherein the localization instrument is configured to be moved relative to the device localization point to at least define a plane of the imaging device;
an imaging device processor in communication with the imaging device to determine a single baseline position of the imaging device based on the plane and a current position of the imaging device relative to the determined single baseline position, wherein the current position is at least one of a plurality of subsequent positions and determined after the determined single baseline position;
an instrument configured to be tracked relative to the anatomy with a tracking system separate from the imaging device;
a navigation processor in communication with the tracking system to determine the position of the instrument relative to the anatomy; and
a display device configured to display an image and an icon representing the instrument at a selected perspective relative to the image on the display device based on the determined single baseline position or determined current position of the imaging device;
wherein the icon is displayed on the display device relative to the image corresponding to the position of the instrument relative to the anatomy and the selected perspective based at least on the current position;
wherein the navigation processor is configured to determine an orientation of the image relative to the anatomy based upon the determination of the current position of the imaging device with the imaging device processor during the acquisition of a second image data at the current position;
wherein the navigation processor determines the position and the selected perspective of the instrument based upon both the determined current position of the imaging device compared to the determined single baseline position of the imaging device and the tracked position of the instrument.

* * * * *